United States Patent [19]

McLaughlin

[11] Patent Number: 4,993,589
[45] Date of Patent: * Feb. 19, 1991

[54] DISPOSABLE ARTICLE DISPENSER

[76] Inventor: David T. McLaughlin, 279 Highgate Ave., Worthington, Ohio 43085

[*] Notice: The portion of the term of this patent subsequent to Jul. 4, 2006 has been disclaimed.

[21] Appl. No.: 365,835

[22] Filed: Jun. 14, 1989

Related U.S. Application Data

[63] Continuation-in-part of Ser. No. 214,060, Jun. 30, 1988, Pat. No. 4,844,293.

[51] Int. Cl.⁵ .............................................. B65H 1/00
[52] U.S. Cl. ...................................... 221/33; 221/56; 221/59; 221/197
[58] Field of Search ....................... 221/33, 45, 46, 56, 221/58, 59, 287, 197

[56] References Cited

U.S. PATENT DOCUMENTS

| | | | |
|---|---|---|---|
| 912,804 | 2/1909 | Brush | 312/50 |
| 1,973,984 | 9/1934 | Hondeville | 221/59 |
| 2,858,045 | 10/1958 | Loeb | 221/59 |
| 3,178,054 | 4/1965 | Lindecker | 221/58 |
| 3,942,682 | 3/1976 | McKay | 221/58 |
| 4,844,293 | 7/1989 | McLaughlin | 221/59 |

Primary Examiner—Andres Kashnikow
Assistant Examiner—W. Todd Waffner
Attorney, Agent, or Firm—Francis T. Kremblas, Jr.

[57] ABSTRACT

A dispensing apparatus for disposable, thin plastic articles is disclosed wherein said articles may be retrieved by the user one at a time in a relatively simple manner. The apparatus comprises a box-like, generally rectangular enclosure for housing a removably mounted packet containing a plurality of the disposable articles stacked in the packet in closely spaced, parallel relationship in a flat condition. The enclosure is provided with a front window or opening and a removable top cover or cap. The packet of articles is loaded into the enclosure through the top opening and are disposed to be removed, one at a time, through the front opening of the enclosure. The packet comprises a pair of faces yieldably connected to one another which have a planar configuration at least as great as the area of the articles disposed between them. The enclosure includes a spring to support the faces of the packet carrying the articles in a parallel relationship to the walls of the enclosure with the faces and the articles being biasly urged toward the front window to conveniently present the outermost article to the user.

5 Claims, 2 Drawing Sheets

U.S. Patent  Feb. 19, 1991  Sheet 1 of 2  4,993,589
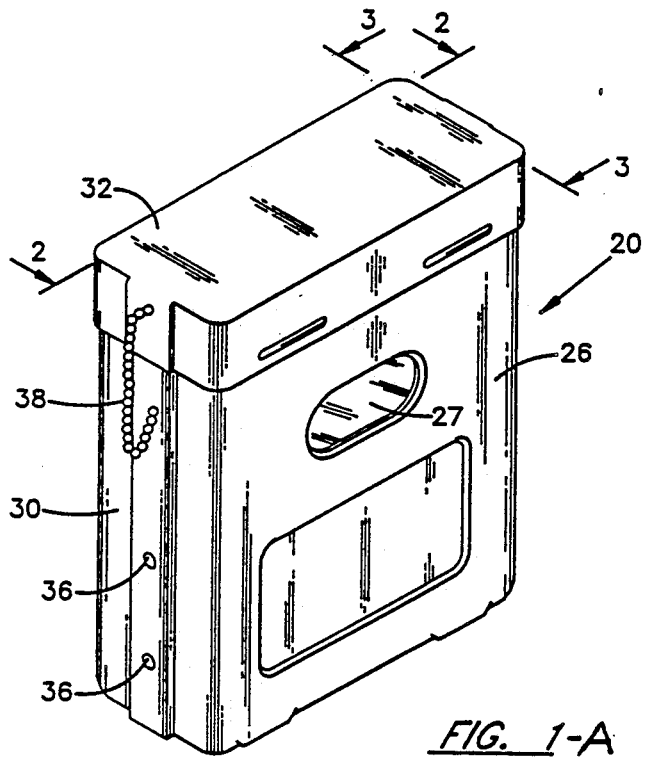
FIG. 1-A
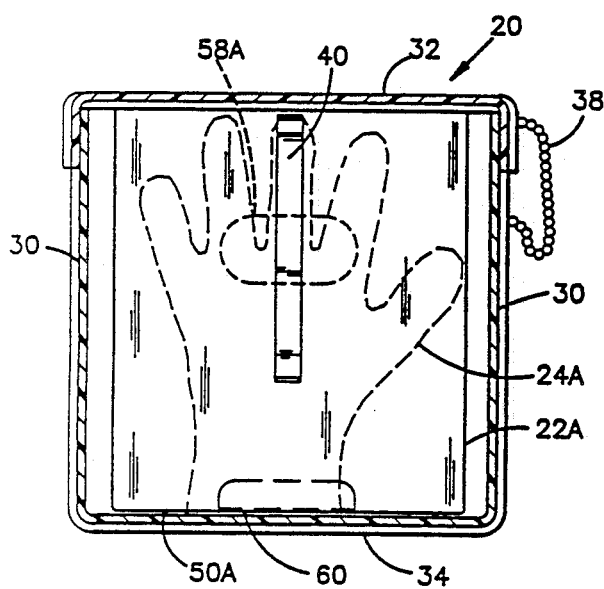
FIG. 2-A
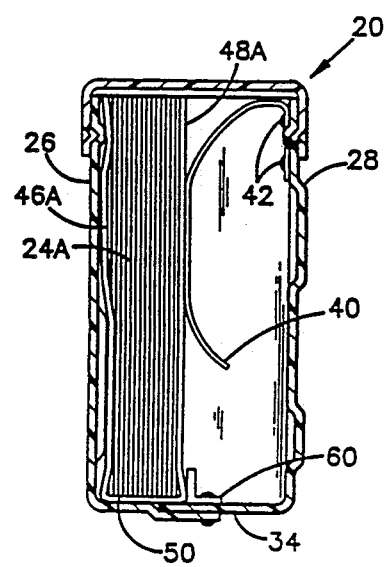
FIG. 3-A

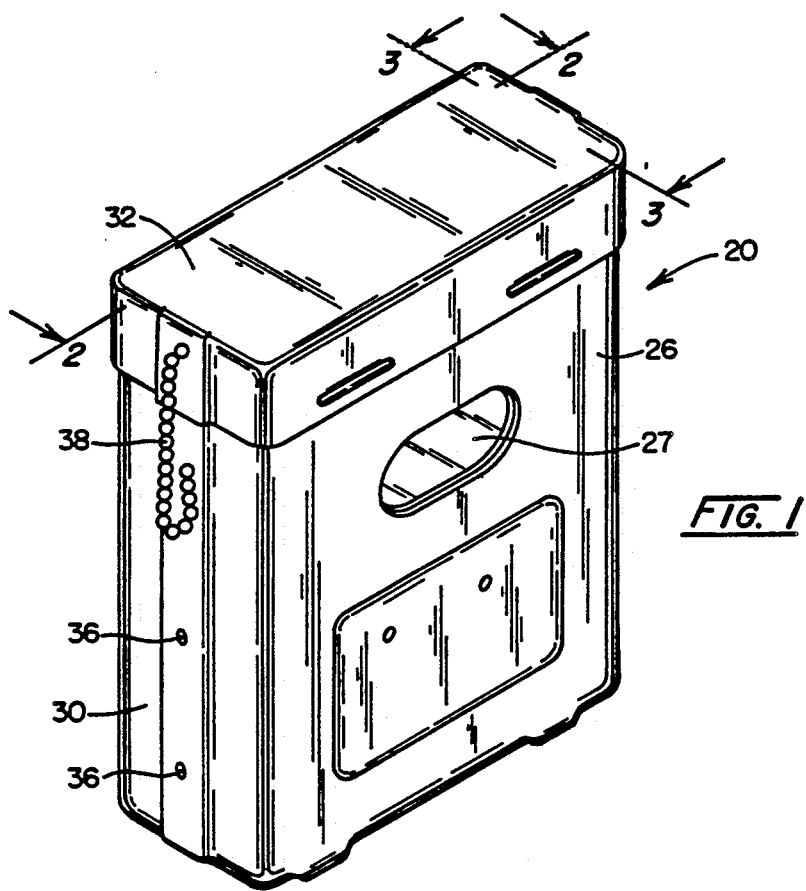
FIG. 1
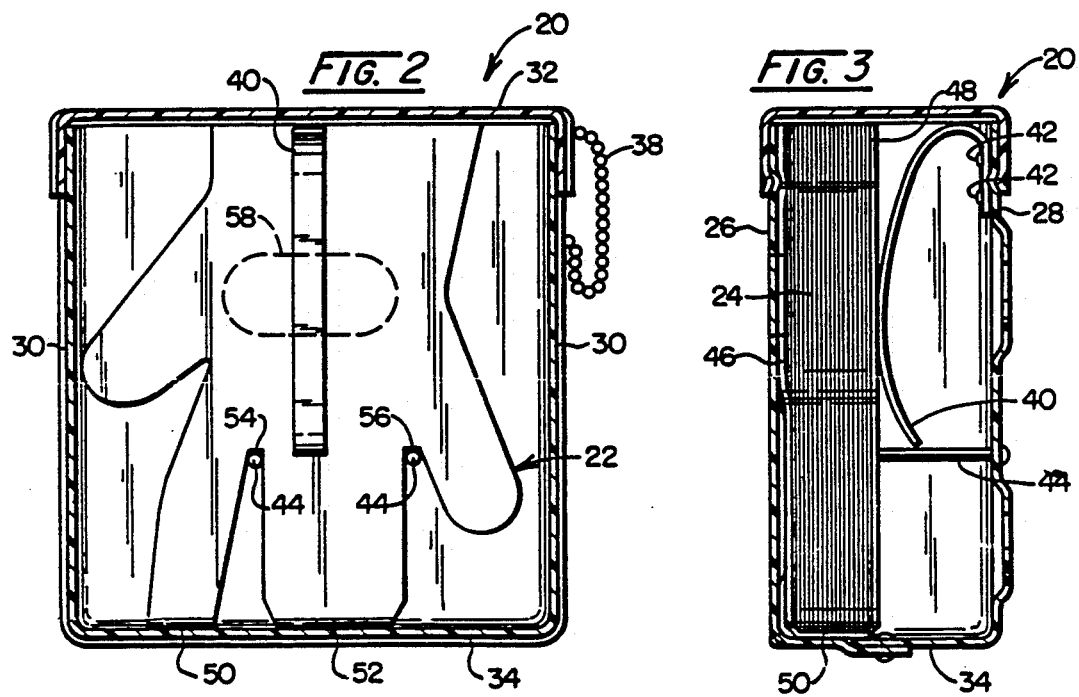
FIG. 2
FIG. 3

DISPOSABLE ARTICLE DISPENSER

This application is a continuation in part of my copending application Ser. No. 07/214,060 filed on June 30, 1988, now U.S. Pat. No. 4,844,293.

BACKGROUND

Relatively thin, disposable articles, such as gloves or other flat, thin articles have a variety of uses and applications in the present marketplace and have been available for many years. However one of the major drawbacks to expanding the use or availability of such articles resides in the manner in which they have been packaged for use or distribution to the ultimate user. Given the intended disposable nature of these articles and the necessity of maintaining a low cost per article, the prior means for packaging a plurality of gloves, for example, in a unit for dispensing consisted of a paperboard box containing a plurality of gloves stacked therein in a folded relationship. The other packaging means for such gloves comprised a roll of tissue paper carrying a single glove mounted on the paper roll in spaced relationship from one another along the length of the roll.

The first described means has been found less than satisfactory because it is very difficult to consistently retrieve only one glove at a time and results in an objectionable percentage of waste. Therefore too often a user pulls a plurality of gloves out of the box resulting in discarding all but the one required. Additionally, the box or container represents a significant cost which is lost when the empty box is discarded. The second means is not satisfactory because it is too costly for many applications or potential applications wherein the gloves otherwise might be made available for rise. Further, both of such methods for packaging such disposable articles for easy dispensing are deficient in providing protection against the elements of weather or against waste due to casual tampering or destruction, thereby significantly hindering the use thereof in outdoor applications.

An additional disadvantage of the common box-type throw-away container is that practical use is limited to the articles disposed horizontally on a horizontal supporting surface rather than in a vertical position hanging from a vertical wall or the like. The latter position is the most desirable in commercial applications to save valuable workspace.

Therefore, the expansion of the use of such disposable articles has been hampered by the lack of a convenient and reliable dispensing package which provides efficient one at a time retrieval of the articles in a low cost manner and further provides a more secure and protected dispensing vehicle which is not so cost prohibitive as to make the use of the articles economically impractical for most applications.

SUMMARY OF INVENTION

The present invention relates to disposable article dispensers in general and particularly to a novel, improved article dispenser for articles disposed in a flat, stacked relationship which promotes efficient dispensing of one article at a time in a relatively low cost manner. As one aspect of the present invention, the disposable articles are packaged in the form of a packet containing a given number of articles. The packet is removably mounted in a relatively secure enclosure from which a glove or other type of article may be retrieved one at a time in a very convenient manner.

In one preferred embodiment, the novel packet includes front and rear faces which are configured generally similar to the configuration of the gloves which themselves are stacked between the faces in a full palm and fingers open, flat disposition. The packet includes a top opening and front and rear faces which are connected or closed at the bottom along the ends thereof commensurate with the middle three fingers of the gloves. The packet also includes a closure supporting the webbing at the base between the ring finger and the little finger and between the middle and index finger which define a stop means limiting the depth the gloves are positioned between the faces of the packet.

As a further aspect of the present invention, the enclosure includes a pair of spaced pins located therein to provide support for the removable packet which in cooperation with the faces of the packet and a leaf spring mounted in the enclosure, dispose the articles in a suitable position to be retrieved through aligned openings in one face of the packet and in a front wall of the enclosure.

Another preferred embodiment provides a similar secure enclosure wherein the opposing faces of the packet, containing the articles stacked in a generally flat planar relationship, are generally rectangular and yieldably connected to one another so that the faces may be biased toward one another when disposed in the enclosure means.

It is therefore an object of the present invention to provide an efficient disposable glove or flat article dispenser which includes a packet containing a plurality of disposable articles removably mounted in a secure enclosure in a manner which promotes easy removal of one article at a time.

It is another object of the present invention to provide a novel packet or package of a plurality of disposable articles wherein the packet is mounted within the protecting enclosure in a collapsible manner to assure that the top article of the stack of articles is always biased against the openings through which the articles are to be removed. This feature provides essentially the same level of ease of removal irrespective of the number of articles remaining in the packet until the last article in the packet is removed.

It is still another object of the present invention to provide a disposable glove or flat article dispenser of the type described wherein a permanent type of outer enclosure and a removably mounted packet of the disposable articles cooperate to position the articles for easy retrieval from a vertical position hanging from a wall surface.

It is a further object of the present invention to provide a disposable article dispenser which includes an outer enclosure providing a significant degree of protection against the elements of the weather to promote use in outdoor applications, as well as withstanding wet conditions such as encountered in food and meat processing applications.

Further objects and advantages of the present invention will be apparent from the following description, reference being had to the accompanying drawings wherein a preferred form of embodiment of the invention is clearly shown.

IN THE DRAWINGS

FIG. 1 is a perspective view of a disposable glove dispenser constructed in accordance with the present invention;

FIG. 2 is a front elevational view, in section, of the dispenser shown in FIG. 1, the section being taken along line 2—2 in FIG. 1; and FIG. 3 is a side elevational view, in section, of the dispenser shown in the preceding Figures, the section being taken along line 3—3 in FIG. 1.

FIG. 1-A is a perspective view of modified embodiment of a disposable glove, which is particularly useful for dispensing form fitting latex or vinyl gloves;

FIG. 2-A is a front elevational view, in section of the dispenser shown in FIG. 1-A, the section being taken along line 2—2 in FIG. 1; and FIG. 3-A is a side elevational view, in section of the dispenser shown in the preceding figures, the section being taken along line 3—3 in FIG. 1-A

DETAILED DESCRIPTION OF THE DRAWINGS

A disposable glove dispenser constructed in accordance with the present invention is shown in FIGS. 1-3 and includes an outer rigid enclosure, indicated generally at 20. A packet or package indicated generally at 22, containing a plurality of gloves 24, is removably mounted within enclosure 20.

Enclosure 20 is preferably made from a conventional plastic material which may be easily manufactured using standard molding techniques and fabricated in a relatively inexpensive manner. However, other types of suitable materials, such as metal, wood or the like which provide sufficient strength and resistance to weather elements for the intended application may be used without departing from the spirit of the present invention.

Enclosure 20 includes front and rear wall means 26, 28, side walls 30, and bottom wall 34. A cover 32 is removably mounted in the form of a cap-like member, however, it could be suitably conventionally hinged or be constructed in any other well-known manner to provide convenient protected access to the top opening of the interior of enclosure 20.

Front wall 26 is provided with a window or opening 27 to the interior of enclosure 20 for access &:o the gloves stored therein as described in detail later herein.

As shown in FIG. 1, enclosure 20 is formed in a box-like configuration from molded half portions which are riveted together such as at 36. Cover 32 merely slides over the front and side walls of enclosure 20. A chain 38 connected to the cover 32 and a side wall 30 merely is for convenience to keep those portions from together when the cover 32 is removed.

The interior of enclosure 20 includes a leaf spring 40 fixed to rear wall 28 by a pair of rivets 42. A pair of horizontally extending, spaced pins 44 are connected between the front and rear walls to support the packet 22 as described later herein.

Packet 22 includes a front face 46 and a rear face 48 which are connected to one another at the ends of the index finger similar to a glove and at the ends of that portion relating to the middle and ring finger of a glove such as seen at 50 and 52. The top portions of each face 46, 48 are not connected to permit easy assembly of the gloves in the packet and so not to interfere with the yieldability of the faces collapsing toward one another where pressure is applied perpendicular to the plane of the faces.

Preferably the faces 46 and 48 consist of inexpensive cardboard type of material which provides a minimum sufficient degree of stiffness to aid in supporting the thin plastic gloves stacked therebetween. The connecting portions 50 and 52 are of the same material and preferably are provided with folds or the like so as not to interfere with the collapsible nature of the packet described above. As will become evident herein, it is important that the faces of packet 22 are constructed to be collapsed toward one another such as to reduce the distance between the faces as the number of gloves therebetween is decreased.

The faces of packet 22 are yieldably connected to one another along an edge defining the webbing between the base of the index finger and the middle finger and at the base between the ring finger and the little finger, such as at 54 and 56. These connections serve to provide a stop to locate the stack of gloves contained between the faces and aid in supporting the gloves to prevent collapse from the desired open palm and finger, planar configuration as seen in FIGS. 2 and 3. Further, the connections 54 and 56 described above also cooperate with pins 44 to support and locate the packet 22 within the enclosure to align opening 27 and a window or opening 58 provided in front face 46 for access to the stack of gloves 24 when the packet is loaded within enclosure 20 in the proper manner.

To properly use the dispenser of the present invention, the user removes cover 32 and loads a packet 22 carrying a stack of disposable gloves 24 into enclosure 20. The packet 22 and gloves 24 are inserted with the finger portions pointed downwardly, as seen in FIG. 2, between the front wall 26 and leaf spring 40 until the connections 54 and 56 rest upon pins 44. With appropriate dimensioning, the openings 27 and 58 are aligned with one another to expose the top glove in the stack of gloves 24. The cover 32 is then replaced and the dispenser is ready to use.

The enclosure 20 may be provided with any appropriate hardware of conventional design so as to permit it to be hung on a wall or the like.

For example, rear wall 48 may include suitable conventional slots or holes adapted to receive a pin-like member fixed to a wall to enable enclosure 20 to be hung from the wall. In other applications, particularly for outdoor use, more secure means may be employed to conventionally position enclosure 20 for convenient use.

Once enclosure 20 is loaded with a packet 22 as described herein, a disposable glove 24 may be easily removed through openings 27 and 58. It is relatively easy to remove the gloves one at a time because the gloves are not in a folded condition and the stack of gloves 24 are biasly urged toward the openings by the pressure of spring 40. Even as the number of gloves in packet 22 decline, the pressure of spring 40 urges the rear face and the remaining gloves 24 toward the front face 46 and the openings 27 and 5B as the faces, in effect, collapse toward one another. This tends to assure the last few remaining gloves 24 are presented to the user in a similar manner as if the packet 22 were full.

When the gloves 24 become exhausted, a new packet 22 of glove 24 may be inserted as previously described after the exhausted packet is simply removed through the top of the enclosure after cover 32 is removed.

Now referring specifically to FIGS. 1-A through 3-A, a modified packet for a glove or article dispensing apparatus is illustrated which is adapted to appropriately store a stack of gloves or other flat articles, for example, disposed in an planar or flat configuration.

Those portions of the apparatus which are substantially of identical construction to the embodiment shown in FIGS. 1-3 are indicated by the same reference numeral with the modified components indicated by the complimentary numeral followed by the letter A.

The modified embodiment shown in FIGS. 1-A through 3-A is particularly well-suited for use with a more substantial type of thin latex or vinyl disposable glove which is more form fitting to the user's hand than the thin polyethylene type described in connection with the embodiment shown in FIGS. 1-3. Further, it is also applicable to planar sheet articles such as disposable hand towels made in a more substantial form than the common paper towels sold in the form of rolls.

This more substantial and form fitting latex or vinyl disposable glove is commonly used in hospitals, physicians offices and nursing homes as well as in some food handling applications. While this more substantial glove would work well using the embodiment described in FIGS. 1-3, it has been found that such gloves can be very satisfactorily supported in a secure manner in the embodiment employing the modified packet or package 22-A as seen in FIGS. 1-A through 3-A. While also applicable to a stack of sheet-like articles such as disposable hand towels, the present invention, for purposes of description, will relate to the latex gloves merely as a preferred example.

Packet 22-A includes parallel planar faces 46-A and 48-A which are disposed in generally parallel relationship to one another and yieldably connected to one another along a generally straight bottom edge 50-A. Preferably, the opposing ends of faces 46-A and 48-A are unconnected to provide easy access to load a stack of gloves 24-A disposed in overlying relationship between the faces in a fully open palm and finger configuration. The latex gloves 24-A are diagrammatically represented as seen in FIG. 2-A.

The configuration of planar faces 46-A and 48-A is preferably rectangular, however other shapes may be used as long as the planar area is substantially fully as great as the planar area of the articles arranged in a flat condition the case of latex gloves, they are arranged in an open palm and extended finger relationship.

Since the type of conventional, well-known, disposable latex glove referred to herein is more substantial than some forms of the loose-fitting polyethylene type, it has been found that the combination of the yieldable faces with the spring bias provided by leaf spring 40 is very satisfactory to maintain the stack of gloves in a parallel, properly aligned position relative to opening 58-A in one of the faces with the window 27 when positioned in enclosure 20.

The faces 46-A and 48-A and the connecting lower edge 50-A may be made of an inexpensive cardboard material. However, it has been found that the material forming said faces must have a reasonable degree of stiffness to support the stack of gloves 24-A in the desired relationship.

If desired, packet 22-A may include a pliant or yieldable connection along the side edges thereof to partially close the sides of the packet to aid maintaining the proper position of the stack during handling and loading into the enclosure 20 through top opening thereof A conventional tape strip which is positioned after the stack of gloves is loaded between the faces during assembly of the packet 24-A would be satisfactory. Alternatively, a light, loose fitting plastic film may be used to enclose the whole of packet 24-A after packet 22-A has been loaded with the stack of gloves 22-A to provide stability and cleanliness. Protection from contamination during shipment, storage, handling and the like is particularly desirable when the gloves are used in applications where sterile conditions are deemed desirable or necessary.

The stack of gloves 24-A is essentially loaded into enclosure 20 in the same manner as previously described for the embodiment shown in FIGS. 1-3.

If a plastic covering is employed, a slit or opening is made in the covering film layer to expose opening 58-A.

Opening 58-A may be formed using a perforated border or the like, not shown, which defines the outer edges of opening 58-A to permit the user to easily tear away the portion of the planar face within the perforated boundary to create the opening 58-A prior to loading the packet into enclosure 20.

Once the packet 22-A carrying the stack of gloves 24-A is loaded into enclosure 20, top 32 is replaced over the top opening of enclosure 20. In many applications, it is highly desirable to mount a disposable article dispenser in a vertical position on a vertical wall or the like in the work place. This positioning is highly desirable to provide ease of access without taking up valuable work, table or floor space in typically space conscious applications.

The dispensing apparatus of both the embodiments described herein are well-suited for vertical disposition of enclosure and the stack of gloves to permit enclosures 20 to be attached to a vertical surface in a convenient to reach manner.

The combination of the supporting packets 22 and 22-A and the force provided by leaf spring 40 assure that the gloves remain aligned with opening 58 or 58-A and window 27 to permit easy withdrawal of the outer most glove without disturbing the remainder of the stack. Further the gloves do not slump or fall out of proper alignment as the stack of gloves becomes smaller as the gloves are removed.

In the preferred embodiment shown, it is desirable to include a L-shaped guide 60 which is attached to the bottom wall of enclosure 20. Guide 60 functions to aid as a guide to the initial positioning of packet 22-A into enclosure 20 and also acts as a stop means to prevent the bottom edge of packet 22-A from sliding rearwardly to any significant degree during use. This provides a positive means to maintain packet 24-A in proper alignment in cooperation with spring 40 even when a relatively thin material is employed to make faces 46-A and 48-A.

Alternatively or in combination with guide 60, leaf spring 40 may be made longer to engage the lower end portion of packet 22-A to aid in preventing any significant degree of rearward sliding of the lower end of packet 22-A which may lead to misalignment of opening 58-A.

In view of the foregoing description, it should be readily apparent that the present invention provides a highly useful and a significant improvement in dispensing disposable articles such as gloves for easy and efficient use.

In view of the foregoing description it should be readily appreciated that a disposable article dispenser is provided which promotes efficient one at a time removal of a thin, flexible article in a very easy fashion. Further, the permanent, sturdy, and re-usable enclosure 20 cooperates with packet 22 to provide the ease of dispensing a single article and yet offers improved protection to promote outdoor use of the disposable gloves. It should be appreciated that a more secure cover or lid, such as 32, could be easily designed using conventional methods where deemed necessary to provide a means for locking the cover in place to discourage unauthorized removal of the whole packet 22 without departing from the present invention.

Additionally, it should be pointed out that the initial cost of the permanent and re-usable enclosure 20 is greatly minimized over a reasonable short period of use so as to add minimal expense on a per article basis over the useful life of the enclosure 20.

I CLAIM

1. A dispensing apparatus for disposable articles comprising, in combination:
   (a) a generally rectangular, rigid enclosure having at least two spaced, parallel extending wall means, a top opening and a window in one of said wall means, said top opening and said window providing interior access to said enclosure;
   (b) a packet having a pair of spaced parallel extending faces yieldably connected to one another, said faces having a planar configuration generally fully encompassing the planar area of an article to be dispensed disposed in an unfolded, planar disposition, one of said faces having an opening aligned with the window of said wall means of said enclosure;
   (c) a plurality of articles mounted in said packet between said faces in a stacked, parallel extending relationship with one another and parallel to said faces of said packet in an unfolded, planar relationship;
   (d) and means mounted in said enclosure for biasing said faces of said packet and the stack of articles toward said window in said wall means to urge the outermost article in said stack closely adjacent to said window.

2. The apparatus defined in claim 1 wherein said faces of said packet are yieldably connected to one another along their bottom edges as defined relative to said top opening of said rigid enclosure to permit said faces to yield toward one another upon application of a force in a direction generally perpendicular to the plane formed by either of said faces.

3. The apparatus defined in claim 1 wherein said means defined in (d) comprise a spring means engaging the planar face of said packet opposite of said face having said opening aligned with said window and a parallel wall of said enclosure to urge said faces toward said window.

4. The apparatus defined in claim 1 wherein said faces of said packet are yieldably connected to one another along an edge of said faces closely spaced to one end of said articles confined within said packet and cooperate with said means for biasing said faces to maintain said articles disposed between said faces in an unfolded, planar relationship and said opening in said packet generally aligned with said window of said wall means of said enclosure.

5. A dispensing apparatus for disposable articles comprising, in combination:
   (a) a generally rectangular, rigid enclosure having at least two spaced, parallel extending wall means, a bottom wall, a top opening and a window in one of said wall means, said top opening and said window providing interior access to said enclosure;
   (b) a packet having a pair of spaced parallel extending faces yieldably connected to one another along an edge, said faces including a planar configuration generally fully encompassing the planar area of an article to be dispensed disposed in an unfolded, planar disposition between said faces, one of said faces having an opening aligned with the window of said wall means of said enclosure;
   (c) a plurality of articles mounted in said packet between said faces in a stacked, parallel extending relationship with one another and parallel to said faces of said packet in an unfolded, planar relationship, one end of said articles being closely spaced to said edge yieldably connecting said faces of said pocket;
   (d) means mounted in said enclosure for biasing said faces of said packet and the stack of articles toward said window in said wall means to urge the outermost article in said stack closely adjacent to said window, said biasing means cooperating with said yieldably connected faces to maintain said articles in an unfolded, planar relationship between said faces and said opening in said pocket generally aligned with said window of said wall means; and
   (e) a vertically extending guide member fixed to an inner surface of said bottom wall and extending upwardly at a location intermediate the parallel extending wall means.

* * * * *